United States Patent [19]

Redington et al.

[11] Patent Number: 4,818,234
[45] Date of Patent: Apr. 4, 1989

[54] PSYCHOPHYSIOLOGICAL REFLEX ARC TRAINING SIMULATOR

[76] Inventors: Dana J. Redington, 630 Park Rd., Redwood City, Calif. 94062; Larry G. Mah, 320 Masonic Dr., East Vallejo, Calif. 94591

[21] Appl. No.: 878,232

[22] Filed: Jun. 25, 1986

[51] Int. Cl.$^4$ .............................................. A63B 69/00
[52] U.S. Cl. ..................................... 434/247; 272/76
[58] Field of Search ................................. 272/76–78; 434/247, 258

[56] References Cited

U.S. PATENT DOCUMENTS

| | | |
|---|---|---|
| 1,170,467 | 2/1916 | Taylor . |
| 3,933,354 | 1/1976 | Goldfarb et al. . |
| 4,027,875 | 6/1977 | Hurley . |
| 4,084,811 | 4/1978 | Kyo . |
| 4,088,315 | 5/1978 | Schemmel . |
| 4,108,428 | 8/1978 | Winterbottom . |
| 4,309,029 | 1/1982 | Tomko . |
| 4,353,545 | 10/1982 | Anderson . |
| 4,365,800 | 12/1982 | Hay et al. . |
| 4,401,303 | 8/1983 | Anderson et al. . |
| 4,440,400 | 4/1984 | Neuberger . |
| 4,534,557 | 8/1985 | Bigelow et al. . |
| 4,564,192 | 1/1986 | Lebowitz . |
| 4,565,366 | 1/1986 | Struss . |

FOREIGN PATENT DOCUMENTS

| | | | |
|---|---|---|---|
| 2725662 | 12/1978 | Fed. Rep. of Germany | ........ 272/76 |
| 2741090 | 3/1979 | Fed. Rep. of Germany | ........ 272/76 |
| 0674751 | 7/1979 | Fed. Rep. of Germany | ........ 272/76 |

*Primary Examiner*—Leo P. Picard
*Attorney, Agent, or Firm*—Flehr, Hohbach, Test, Albritton & Herbert

[57] ABSTRACT

The present invention provides an apparatus and method for evaluating the psychophysiological reflex arcs. Unique to this invention is the trichotomy of a reflex into Sense-Decide-Act Loop. The invention embodies knowledge about stimulus presentation, the monitoring of striking behavior, and in the evaluation of three reflex phase times. Optionally, the type of strike, e.g., punch, jab, block, kick, and physiology, i.e., the characteristics of the sensory/motor pathways, are used to gain a more accurate assessment of reflex performance rather than merely using the absolute length of reaction time. Decision making by the trainee, also, more closely approaches "worldly" combative/competitive situations by adding complex stimuli that must be discriminated among each other in comparison to the mere triggering of lights or other sensory stimuli. The apparatus is self contained in the single-chip microcomputer version. More elaborate testing configurations can be applied to testing one or more trainees in the microcomputer version using a personal computer.

19 Claims, 7 Drawing Sheets

1a

PSYCHOPHYSIOLOGICAL REFLEX ARC TRAINING SIMULATOR

BACKGROUND OF THE INVENTION

1. Field of the Invention

This invention relates generally to a psychophysiological reflex training system and more particularly to an apparatus and method for testing and evaluating striking behavior associated with martial arts and other competitive/combative sports situations.

A variety of training methods have been used in the past to train striking behavior by means of reaction time type tasks. The goal of such methods is generally to present a (pseudo) random signal, to monitor the trainee's striking behavior, and then provide feedback to the trainee on his/her performance. The signal is usually the onset or offset of a visual stimulus, such as a light or group of lights, the onset or offset of an auditory stimulus, such as, a tone emitted from a buzzer or speaker, or the thrust of some physical object (such as a sword or shaft). When the trainee notices the presentation of the stimulus, he/she is supposed to perform some striking behavior. Striking behavior is usually a jab, punch, block, or kick, that results in impacting the target with varying degrees of speed and force. Two general parameters of striking behavior are usually evaluated and fed back to the trainee: simple reaction time and force of the strike. Simple reaction time is the length of delay in seconds between the presentation of a signal and the striking behavior. Force is the measured pressure at the target of the striking behavior.

2. Prior Art

The basic theory behind psychophysiological processes is explained with a physiological emphasis in West (Best and Taylor's Physiological Basis of Medical Practice. Baltimore: Williams & Wilkins 1985; Chapters 3 and 4 and Section 9). An emphasis in the physiological processes is explained in Tart (States of Consciousness. New York: E. P. Dutton & Co., Inc. 1975; Chapter 2).

Current state-of-the-art approaches to systematic measurement of striking performance based on reaction times (Biglow et al., U.S. Pat. No. 4,534,557; Goldfarb et al., U.S. Pat. No. 3,933,354; Schemmel, U.S. Pat. No. 4,088,315) have not estimated performance by taking into account the difficulty of the test. Previous approaches (including Taylor, U.S. Pat. No. 1,170,467; Hurley, U.S. Pat. No. 4,027,875; Kyo, U.S. Pat. No. 4,084,811; Winterbottom, U.S. Pat. No. 4,108,428; Tomko, U.S. Pat. No. 4,309,029; Anderson, U.S. Pat. No. 4,353,545 and U.S. Pat. No. 4,401,303; Hay et al., U.S. Pat. No. 4,365,800; Neuberger, U.S. Pat. No. 4,440,400; Lebowitz, U.S. Pat. No. 4,564,192; and Struss, U.S. Pat. No. 4,565,366) have not used discriminative stimuli of varying complexity that require the trainee to mentally evaluate the occurrence of a predefined target sequence of varying difficulty before initiating and completing a pre-specified motor behavior, such as striking. The prior art patents have not utilized a method that incorporates numeric data about type of sensor/motor activity in order to estimate minimum response times and then evaluate performance. The knowledge of sensory/motor activity requires an understanding of psychophysiology which delineates the minimum delays in time associated with the type and length of sensory and motor pathways associated with a specific striking behaviors and on the specific instructions given to the trainee to perform that striking behavior. While the prior art (Bigelow et al.) has used force sensing, a fully digital approach has not been incorporated into a single device such as the present invention; nor have audio feedback proportional to degree of force or a vertical array of feedback lights been used. While the prior art (Goldfarb et al.) has used a general target figure with a complex back-lit switch or a complex body figure attached to a separate control panel (Schemmel), the present invention incorporates specific marked (not back-lit) cellular targets; by merely increasing the number of targets different positions can be incorporated into a test of increasing complexity rather than subdividing a single complex target or figure into smaller striking areas.

SUMMARY AND OBJECTS OF THE INVENTION

The present invention provides a means of developing and increasing reflexive neuromuscular performance under controlled conditions. The controlled conditions simulate time-sensitive combative/competitive situations, e.g., striking an object or fighting an opponent, while minimizing, if not totally eliminating, the danger of sustaining neurological and physical damage of those situations. The object of reflex training is to respond, as quickly as possible, to the presentation of a (discriminative) stimulus by performing a predefined behavior which results in striking a pad. A microcomputer controls stimulus presentation, evaluates strikes to a pad, and generates feedback on reflex performance. Specific types of strikes, e.g., punches, jabs, blocks and kicks, are monitored for accuracy, speed, and optionally, power. Performance is based on four components: speed of responding, and optionally, consideration to the physical size of the trainee, the type of strike being practiced, and the amount of force delivered to the pad. The components are used to calculate the trainee's ideal or perfect psychophysiological reflex response. Trainee's performance is compared to the perfect psychophysiological reflex and feedback is given visually, and/or optionally auditorily, to indicate the immediate level of the trainee's reflexes.

It is a primary object of the present invention to provide an improved reflex evaluation and an improved reflex training system.

Another object of the present invention is to provide techniques for reflex training using available microprocessor technology.

In accordance with these objectives the present invention provides an apparatus and method for training psychophysiological reflexes in accordance with the type of striking behavior being practiced and with the type of contigent stimulus used to initiate behavior.

The invention will be more readily apparent from the following detailed description when taken in conjunction with the drawings, in which.

DETAILED DESCRIPTION

Figure 1:
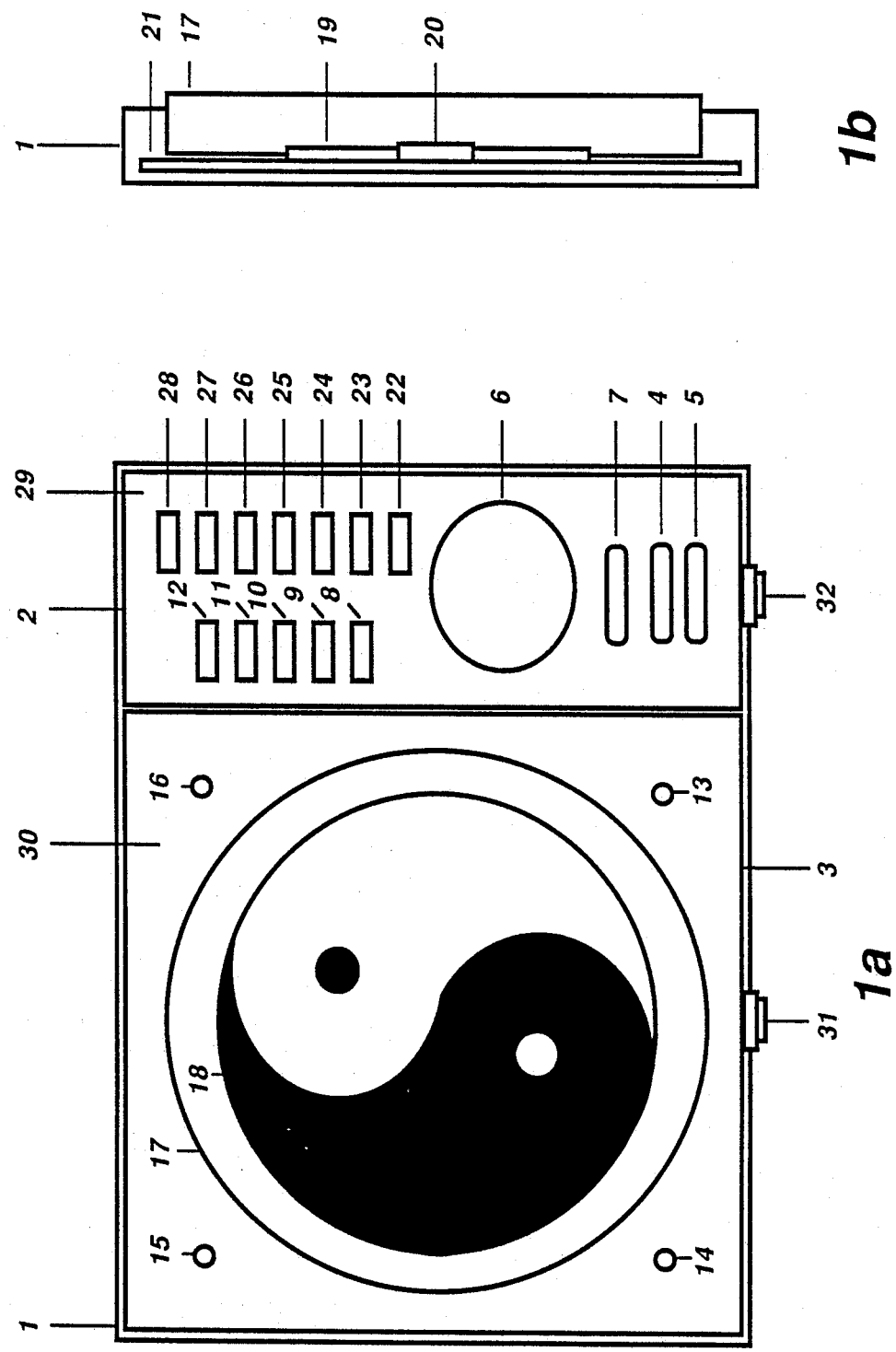
FIG. 1 shows a preferred embodiment of a training system used for evaluating striking behavior.

FIG. 1 shows a self-contained psychophysiological reflex training simulator 1 generally including a controller/feedback unit 2, and a pad/sensor unit 3. The controller/feedback unit 2 provides a means for turning the training system 1 on via an on/start switch 4 or off via an off/stop switch 5.

Once the system 1 is activated by depressing the on/start switch 5, the controller generates an introductory auditory prompt, " . . . Depress ON to start or depress DIFFICULTY to set test parameters.", via the speaker 6. The level of difficulty and other test parameters are set via the set-difficulty switch 7 unless the default or start-up level and parameters are desired. The controller 2 prompts the trainee with short auditory commands via the speaker 6. First, the controller 2 prompts "Set body size: one small, two medium, three tall, or four extra-tall. Then hit ON". One to four key depresses of the set-difficulty switch 7 establishes the current body size. Upon depressing the on switch 4 the controller 2 prompts with "Currently<current.size>- body type.", a short pause, and then prompts "Enter strike: one punch or two kick. Then hit ON". One or two depresses of the set-difficulty switch 7 establish the current strike type. Upon depressing the on switch 4 the controller 2 prompts with "Currently<current.- strike>strike type.", a short pause, and then prompts with "Enter test mode: one visual, two auditory, or three both. Then hit ON." One to three depresses of the set-difficulty switch 7 establish the current test mode. Upon depressing the on switch 4 the controller 2 prompts with "Currently<current.mode>test mode.", a short pause then "Enter number of trials: one for ten, two for twenty-five, three for fifty, or four for one hundred. Then hit ON." One to four depresses of the set-difficulty switch 7 establish the number of trials. Upon depressing the on switch 4 the computer prompts with "Currently<trials>trials.", a short pause, then "Enter difficulty level: one beginner, two intermediate, three advanced, four expert, or five master. Then hit ON". One to five key depresses of the set-difficulty switch 7 establish the current difficulty level. Upon depressing the on switch 4 the controller 2 prompts with "Currently at<difficult-level>difficulty level.", a short pause then "Press ON to start test or OFF to stop." Difficulty level is also shown in one of five level-indicating light emitting diodes (LEDs); beginner 8, intermediate 9, advanced 10, expert 11, master 12. Upon start-up test parameters default to a medium body type, a punch strike type, visual only test mode, twenty-five trials, and the beginner level of difficulty.

After having optionally adjusted the test parameters, a training test is initiated by a key depress of the on/start switch 4; a training test is stopped by depressing the off/stop switch 5.

The signal or stimulus LEDs 13, 14, 15, and 16 provide a visual reaction time stimulus. The visual reaction time stimulus ranges from (a) a beginner-level, the change from continuous off to continuous on in any color, e.g., bi-color LEDs generate red and green; (b) to intermediate level, the change from a pulsed on/off primary color to a pulsed on/off secondary color with or without an increase in the rate of stimulus presentation, (c) to advanced level, the change in a blinking primary color to a blinking secondary color, (d) to expert level, the change in blink frequency from a primary frequency to a secondary blink frequency in one color, and (e) to master level, the changein a primary frequency to a secondary blink frequency in a secondary color with or without increases in stimulus presentation rate. The blink rate and dwell time (amount of time off and amount of time on within one blink cycle) of the LEDs is arbitrary as long as it is below the Critical Flicker Fusion Frequency of ~30 Hertz; reasonable blink frequencies range from 5 Hertz down to 0.25 Hertz. The change in blink frequency as a rection time stimulus is accomplished by speeding up the frequency to a faster level, i.e., doubling the blink rate. Increases in stimulus presentation are accomplished by reducing the delay time in the inter-stimulus interval.

Auditory reaction time stimuli are equivalent to the visual ones; instead of two color LEDs a high and low tone are used, and varying volume is used to produce changes in the pulse characteristics of the tone.

After a suitable delay in time, the reaction time stimulus is activated: the LEDs 13-16 are turned on or they begin blinking in a secondary color, e.g., green, at the same blink frequency, or a change in blink frequency occurs; and/or, the audio stimulus is presented. At this point, it is up to the trainee to sense the reaction time stimulus and strike the pad 17 in the labeled target area 18. The pad 17 is a rubber-like material to partially absorb the force of the strike and thus minimize trauma to the trainee's body. The target area 18 is painted or embossed with a target symbol to outline where strikes should be placed. On the back side of the pad 17 within the target area 18 is a strike sensing area 19 and a smaller pressure sensing area 20. The strike sensing area 19 is a flat press that closes upon an impact to the pad 17. The smaller pressure sensing area 20 is a pressure transducer, e.g., straing guage, that creates a change in a measurable electrical quantity, i.e., voltage, current, or resistance, proportional to the amount of force of the strike impacting the pad 17. When the trainee strikes the pad 17 the reaction time stimulus is reset reverting to a baseline state; for example, either the LEDs 13-16 are turned off, revert to a primary color, or change back to a primary blinking pattern. An etched circuit board 21 holds the electrical components, such as, press switch 19 and pressure transducer 20.

Immediately following the reset to a baseline state, feedback is given to the trainee by selectively turning on the performance display LEDs 22, 23, 24, 25, 26, 27, 28. LEDs 22-28 indicate the proportional scaled delay in time between stimulus onset and behavioral activation of the strike sensing switch 19. Optionally, LEDs 8-12 are used to indicate a proportional scaled level of force measured from the pressure sensing transducer 20. An additional and optional form of audible feedback is generated at the speaker 6 whose characteristics, e.g., tone and volume are proportional to the speed and force of the strike, respectively; for example, the controller 2 generates a grunt, groan, or other sound. The controller 2 optionally generates a prompt "Elapsed time<number>miliseconds . . . ".

The reflex training test is repeated a number of times, 10 to 100 repetitions constituting a set. Typically after each set, the test is stopped by depressing the off/stop switch 5. The computer generates the command "Average elapsed time of <number>miliseconds.", a brief pause and "Take a break then hit ON to continue or OFF to stop." A brief rest usually 30 to 60 seconds long intervenes and then the test is re-activated by depressing the on/start switch 4. An average reflex training session is made up of five to eight or more sets for one particular type of striking behavior. At the end of a training session the off/stop switch 5 is depressed a second time and the reflex training system is turned off or goes into a low power consumption mode until the next time that the on/start switch 4 is pressed.

The reflex training system's outer shell 29, 30 is physically made of high strength molded plastic with arbitrary coloring, e.g., black, red, blue, and white. The pad/sensor unit 3 can be detached from the controller/feedback unit 2 and linked via a digital interface connector 31 to a detached controller/feedback unit 2 via a controlling digital interface connector 32.

Figure 2:
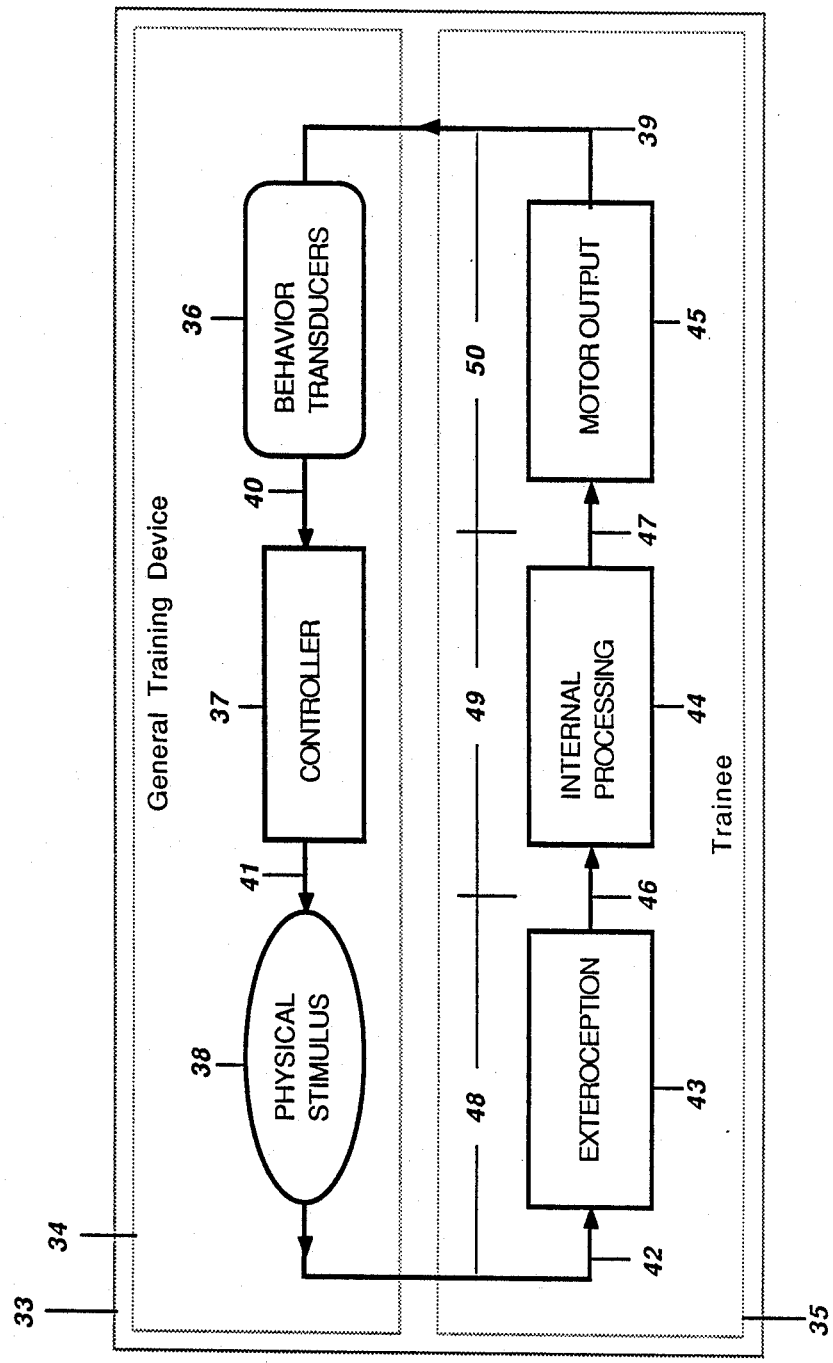
FIG. 2 is a schematic diagram of a psychophysiological training system.

Competitive/combative human behavior in a training system 33 can be simplistically described in terms of psychophysiological components shown in FIG. 2. The training shown generally by block 33 can be divided into a general training device 34 and a trainee 35.

The general training device 34 has three components: behavior transducers 36, a controller 37, and physical stimulus or stimuli transducers 38. Behavior transducers 36 are merely a means of converting the trainee's behavior 39 into electrical signals 40 that are processed by the controller 37; examples of behavior transducers 36 are the strike sensing switch 19 and the force sensing area 20 of the Pad/Sensor unit 3 in FIG. 1. The controller 37 is a microelectronics device, such as a single-chip microcomputer or microprocessor set, that can examine and evaluate electrically converted behavior 40 and then generate electrical feedback signals 41 to stimuli transducers 38. Stimuli transducers 38 convert electrical signals 41 into physical stimuli 42 that are perceptually registrable to the trainee 35.

The trainee 35 is the second part of a psychophysiological training system 33 and can be conceptually divided into three major subsystems: Exteroception 43, Internal Processing 44, and Motor Output 45. Exteroception 43 is one of two sub-systems that connect the trainee to the word (Tart, op cit). Here, stimuli 42 are converted into physiological signals or information 46 and travel to the brain. Internal Processing 44 occurs within the brain and covers the "internal world" and for simplicity includes the subsystems of Memory, Sense of Identity, Subconscious, Emotions, Space/Time Sense, with emphasis on Input Processing, Awareness and Evaluation in-line with Tart's psychological "subsystems of consciousness" perspective. Decisions 47 are one end product of Internal Processing 44. The third sysbsystem is Motor Output 45 and represents the translation of decisions 47 into physical action produced by the body 39. The physiology of Exteroception 43 and Motor Output 45 are understood enough to enable estimating their temporal characteristics, i.e., their estimated delays in time.

In competitive/combative situations, the process of striking is a human behavior that has components which relate to Exteroception 43, Internal Processing 44, and Motor Output 45 in the form of a three phase reflex arc. The psychophysiological reflex arc is divided into a sense phase 48, decide phase 49, and an act phase 50.

The sense phase 48 of the reflex arc relates to Exteroception 43 and involves the trainee monitoring the "world" through the senses with emphasis on visual, auditory, and somatosensory processes. The physiology of the nervous system determines the delay in time between the occurrence of a physical event (an evoking stimulus) and a representation of that event reaching the brain. The sensory phase delay in time can be estimated from the onset of the evoking stimulus and the parameters of the sensory pathway (length and sensory type). For example, a pin prick or a somatosensory event occurring at the index finger will propagate to the brain at a speed equal to the sensory nerve conduction velocity; the sensory phase delay for a somatosensory event will be approximately equal to the conduction velocity multiplied by the estimated length of the afferent nerve pathway to the brain. For simplicity, the sensory phase delay time is divided into one of four estimates based upon the trainee's body size (small, medium, large, and extra-large) multiplied by a numeric constant for sensory type (visual or auditory).

The decide phase 49 of the reflex arc relates to Internal Processing 44 and involves the trainee evaluating incoming stimuli against pre-specified conditions and then deciding with some degree of conscious awareness when an action (strike or other motor output) should occur. A rudimentary decision phase 49 is to decide when a stimulus has occurred (referred to as a simple reaction time stimulus), e.g., when a light has been turned on or off. A simple reaction time task requires a minimum of Internal Processing time. Unfortunately, simple on/off stimuli rarely occur in unarmed combative/competitive situations. More complex decision phase times are associated with discriminating among changing patterns of stimuli of increasing difficulty; for example identifying when a light changes color, when a tone changes in pitch, or when a blinking light changes in blink rate. The result is increases in time for Internal Processing 44. Changes in patterns of stimuli may approximate real combative-/competitive events. For example, the boxer must decide the right moment to make his move: he must discriminate where and where there is an opening in order to deliver a critical punch to an opponent. This situation is simplistically analogous to discriminating a stimulus pattern composed of a blinking light in a primary color interspersed with a randomly presented blinking light of a different color. The blinking light of a different color symbolically represents the "opening" at which to act; the change in color becomes a more lifelike sensory event to be discriminated in comparison to merely recognizing the simple onset or offset of a light.

The act phase 50 of the reflex arc relates to Motor Output 45 and involves performing an observable action 39. Usually the observable action 39 is a motor movement, such as a punch, jab, block, or kick. As in the sensory phase 48, the act phase 50 delay time can be objectively estimated from the time of strike and the type of striking behavior which is directly related to the size of the trainee and which muscles are used for the strike. For example, a right hand punch to a pad is initiated by a subjective command in the brain and propagates down the motor pathways through motor endplates and results in the contraction of a group of muscles that present the hand to the pad. The act phase 50 delay can be estimated by the conduction velocity of the motor nerve multiplied by the length of that pathway. For simplicity, the act phase delay time is divided into one of four estimates based upon the trainee's body size (small, medium, large, and extra-large) multiplied by a numeric constant representing average conduction velocity delay time for a punch or kick.

The psychophysiological reflex arc, i.e., 42-43-46-44-47-45-39, can be summarized as the Sense-Decide-Act Loop. The parameters of the Sense-Decide-Act Loop can be used to monitor performance and generate feedback to the trainee on striking behavior. The total time for a reflex arc reaction is a combination of the time required for sensing 48, deciding 49, and then acting 50. Reflex time can be estimated by objectively controlling the time of stimulus presentation 42 and monitoring the behavioral response 39 time. True contingent striking behavior cannot physically be less than the total time required for a stimulus to the brain which is the delay in sensing phase 48 and the time required for motor impulses to activate the striking behavior which is the delay in the act phase 50. More accurate reflex time can be estimated by using stimuli of varying complexity and difficulty and knowing the length and types of sensory/motor pathways used in performing a psychophysiological reflex arc. The amount of Internal Processing is directly related to the differences in performance between simple and more complex discriminative reaction time tests given with respect to a particular sensory and motor pathway. Thus, elapsed time of the decide phase 49 can be calculated by subtracting out the (average) elapsed times of performance of lesser difficulty from the current level, providing that the trainee performs the same type of striking behavior. As a result more accurate feedback can be given to the trainee to help achieve optimum performance in each phase of the psychophysiological reflex arc by giving him/her estimates of Internal Processing based upon the differences in complex or discriminative reaction times relative to simple reaction times.

Figure 3:
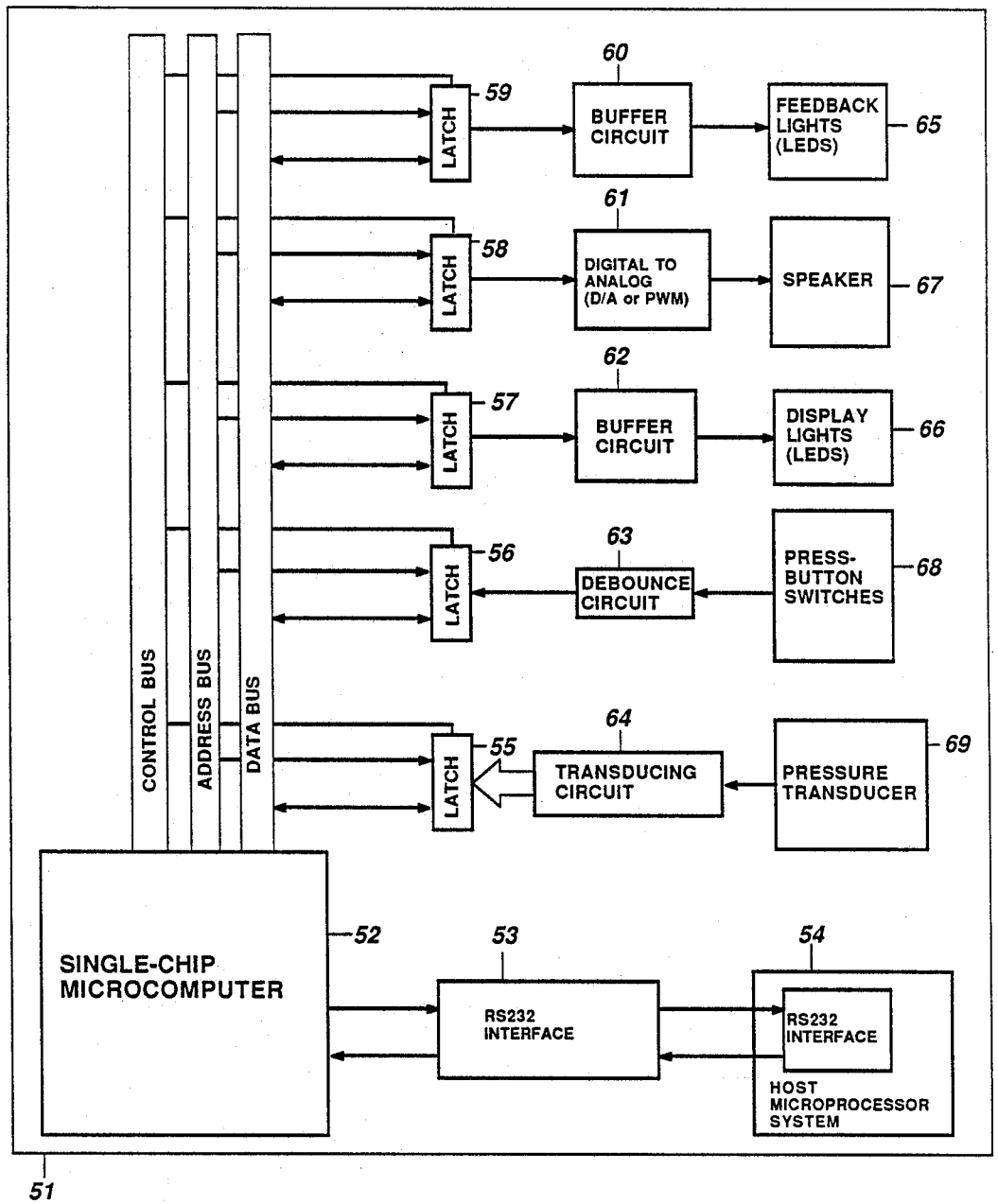
FIG. 3 is a block diagram of a reflex training system incorporating a microprocessor as a controller in accordance with the present invention.

FIG. 3 shows the preferred embodiment of the training simulator 51. The training simulator is composed of a single-chip microprocessor/microcomputer 52. It may be connected by a serial interface 53 to an, optional, host microprocessor system 54. Control, address and data busses are connected to interface latches 55, 56, 57, 58, and 59. Through buffering circuits 60, 62 or transducing circuits 61, 63, 64, connect the latches to visual displays 65, 66, audio output 67, switches 68, and pressure transducers 69, respectively.

The single-chip microprocessor/microcomputer 52 contains a read only memory (ROM) or other "permanent" memory, such as an erasable programmable read only memory (EPROM). The "permanent" memory contains prerecorded computer programs and data including digitized phrases used by the single-chip computer 52 to monitor striking behavior, generate test setting requests, to evaluate striking behavior, and to generate feedback to the trainee on his/her performance. The single-chip computer 52 is able to read and write to specific memory/port locations which are latched 55-59 and may have address decoders associated with them.

Five general types of function are incorporated in the training system 51: visual feedback 65, audio feedback 67, visual stimuli 66, switch sensing 68, and strike pressure sensing 69. For generating feedback either a visual 65 or an auditory 67 circuit is used. In the case of feedback lights 65, LEDs are connected to a buffer circuit 60 composed of a buffering latch, such as, commercially available latches 74LS75, where the input to the buffering latch is controlled from the memory/port addressing latches 59. In the case of audio 67 feedback, a small (2.5 inch diameter or larger) speaker 6 is driven by an integrated amplifier, e.g., LM-380 or other suitable amplifier, whose input is either a digital pulse with modulated (PWM) signal or a simple voltage generated from a digital to analog (D/A) converter. The PWM input can be generated under software control by the single-chip computer 52, merely sending a single bit values, i.e., "0" or a "1" of variable duration through the memory/port addressing latch 58. The D/A converter can also be set through a similar latch 58, although in this case a byte or byte values set the level.

For stimulus presentation control of the bi-color display LEDs 66 uses similar buffer circuitry for 62 as found in 60. Sensing a strike and controlling the single-chip computer 52 is accomplished by press-button switches 68 which trigger a debounce circuit, such as a 74LS132 quad-schmidt trigger, if necessary. The debounce circuit 63 is interfaced to memory/port addressing latch 56 and is read by the single-chip computer 52. Sensing the force of a strike is accomplished by a pressure transducer, such as a resistive strain guage which inputs into an analog to digital converter (A/D) or modifies a frequency base (shift) of an oscillator (FSK). The single-chip computer 52 reads the memory/port address latch 55 for one or two bytes from an A/D converter or counts the number of pulses within a period and calculates the frequency from the FSK. Either the A/D value or the calculated frequency are proportional to force of the strike delivered to the pressure transducer 69.

The single-chip computer 52, optionally, interfaces to a host computer system 54 via a serial (RS-232) port 53. The host microprocessor system 54 is a personal computer, such as the Apple II, Commodore C128/64 or Amiga, Atari 520 ST or 1040 ST, Apple Macintosh, IMB PC or equivalent compatibles, or other suitable computer system.

There are four embodiments of the reflex training simulator 51 incorporating a single chip computer: (1) to use "off the shelf" single-chip microprocessors/microcomputer (such as Intel's MCS-48, MCS-51, MCS-96, or MCS-86 families, Zilog Z8, or Motorola 680x or 14680x families) which incorporate EPROMs; or (2) to use mask programmed ROMs (from the same or similar families); (3) to use a custom chip or chip set that is functionally equivalent to (1); or, (4) to use RAMs in conjunction with a single-chip microprocessor that is down-loaded from a host microprocessor system with a functionally equivalent program in (1).

Figure 4:
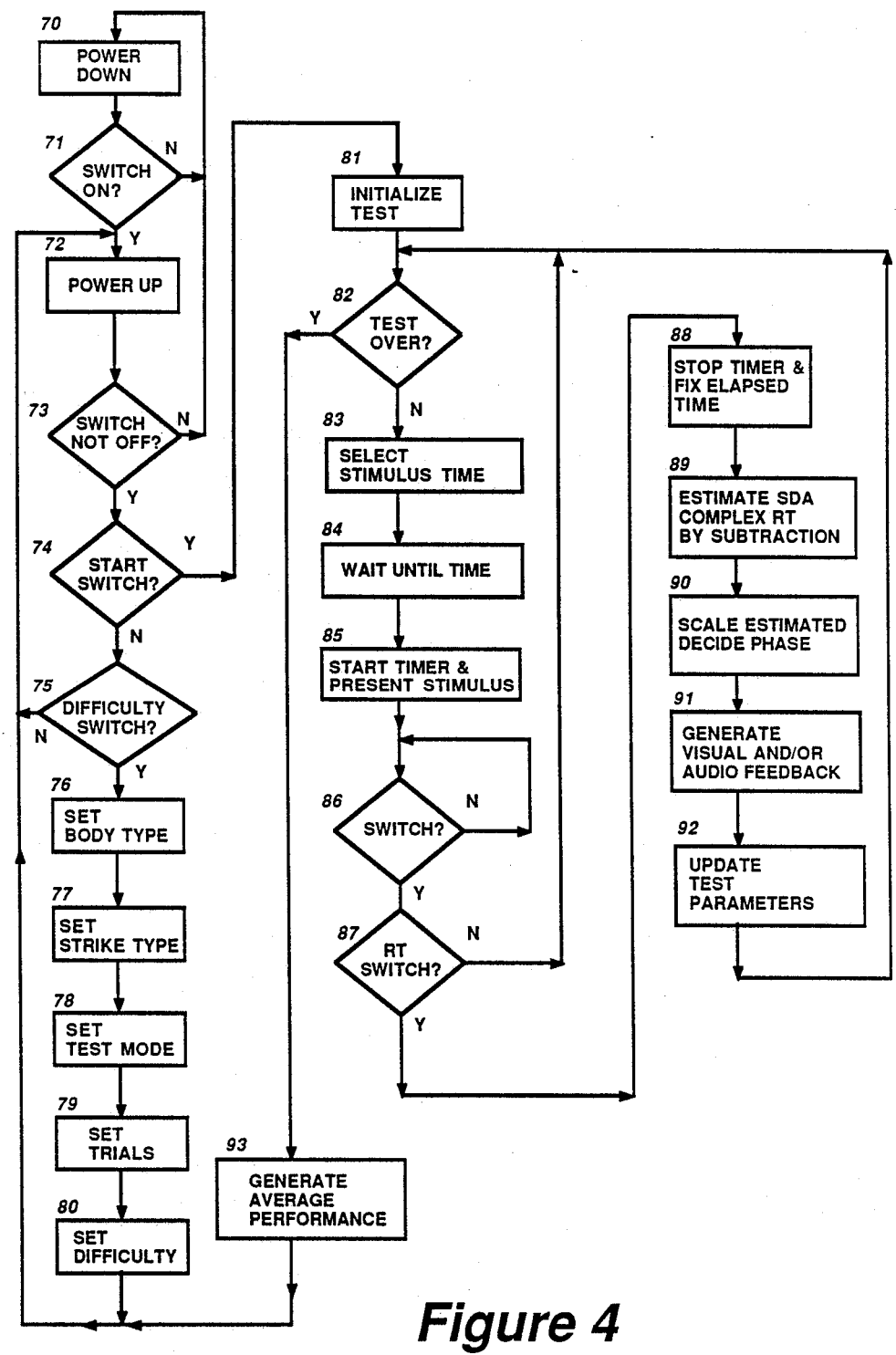
FIG. 4 is a flow chart of a reflex training program.

FIG. 4 shows a general system flow chart which is useful in understanding operation of the training system 51. In a power down 70 state the single-chip computer 52 monitors the on/start power switch 4 FIG. 1, or incoming data from a host computer 54 via the interface 53. If the single-chip computer 52 determines 71 that the on switch 4 has been activated then a power up procedure 72 occurs. During power up 72 the configuration of the reflex training system 51 is checked and necessary adjustments made; if the host computer 54 is present then the single-chip computer 52 follows commands presented via the serial port 53 otherwise it monitors the off 5, start 4, and difficulty 7 switches by decisions 73, 74, 75, respectively. If a off switch 5 is depressed then the single-chip computer 52 returns to a power down state 70.

A depress of the difficulty switch 7 results via 75 in the computer 52 setting test parameters including body type (small, medium, tall, extra-tall) 76, strike type (punch or kick) 77, test mode 78 for audio 6 and/or visual 13-16 stimulus type, number of trials (ten, twenty five, fifty, or one hundred) 79, and test difficulty level (beginner, intermediate, advanced, expert, master) 80. In the case of setting test difficulty, one of five levels is set: a beginner test results in setting the stimulus to a change from continuous off to continuous on in one color of bi-color LEDs 13-16; a intermediate test results in the change from a pulsed primary color to a pulsed secondary color; an advanced test changes to a blinking light in one color to a blinking light in a second color; an expert test fixes the change in blink frequency of a light from lower frequency to a higher frequency; and a master test results in changes of blink frequency in a secondary color with or without an increase in stimulus presentation rate. The current level of difficulty is then shown in LEDs 8-12 FIG. 1.

A start switch 4 results in the computer 52 through decision 74 beginning a test sequence in which the test is initialized 81; unless otherwise set, either manually by steps 76-80 or by host computer 54, all parameters relating to reflex type, trainee size, stimulus type, and test conditions, default to standard (preset) values. The computer 52 repeats the test, decision 82 which checks for test parameters, by selecting a (pseudo) random stimulus time 83, waits the required time 84, then sets the start timer in 52 and presents a stimulus 85 via either lights 66 or speaker 67, waits for a switch depress 19 through decision 86, checks the appropriate switch reaction type 87, and either exits through 82 or stops the timer 88 in the computer 52. The resulting value in the timer represents Sense-Decide-Act 48-49-50 elapsed reaction time. The computer 52 then evaluates the elapsed time in relation to a minimum reaction time estimate of a combined sense-act phase (48 plus 50) either using default/current test values or more accurate numeric data as established by the host computer 54. A true contingent reaction time must be longer than the time it takes for a stimulus to be processed by Exteroception 43 and Motor Output 45. Providing that the elapsed reaction time is a valid number, that is greater to the minimum estimates for sensing 48 and acting 50, the computer 52 estimates 89 the Decide components 49 by subtracting averaged reactio time estimates of Sense-Decide-Act reflex time of the lesser difficulty levels from the current level elapsed time; otherwise, an error light 22 or error message, " . . . You are anticipating . . . ", via 6 is generated and the test is repeated. The resulting Decide component 49 time is then scaled to one of seven levels 90. The computer 52 generates feedback 91 and displays the scaled reaction time on LEDs 22-28 or presents audio feedback at speaker 6. Test parameters are updated, such as incrementing the trials, and calculating the average performance 92 and the computer 52 repeats 82-92 until the test is over. When the test is completed average performance data is presented 93 to the trainee 35.

A typical usage scenerio for the training simulator 1 FIG. 1 using the program flow of FIG.4 follows: Assuming this is a first time usage, the trainee 35 depresses the on/start switch 4. The computer 52 in a power down state 70 checks 71 the on switch 4 and proceeds to a power up state 72 and turns on LEDs 13-16 and/or generates an opening message "Depress ON to start test or depress DIFFICULTY to set test parameters" via the speaker 6. Following power up 72 the computer 52 cycles through three decisions 73-75 waiting for either, a depress of the off switch 5, a depress of the on/start switch 4, or a depress of the set-difficulty switch 7.

Continuing, the trainee depresses the set-difficulty switch 7. The computer 52 advances prompt "Set body size: one small, two medium, three tall, or four extratall. Then hit ON" and the trainee 35 first depresses the set-difficulty switch 7 two times and then depresses the on switch 4. The computer 52 prompts with "Currently medium body type.", a short pause, and then prompts "Enter strike type: one punch or two kick. Then hit ON". The trainee 35 depresses the set-difficulty switch 7 one time and then depresses the on switch 4. The computer 52 prompts with "Currently punch strike type.", a short pause, and then prompts with "Enter test mode: one visual, two auditory, or three both. Then hit ON." The trainee 35 depresses the set-difficulty switch 7 one time. The computer 52 prompts with "Currently visual test mode.", a short pause then "Enter number of trials: one for ten, two for twenty-five, three for fifty, or four for one hundred. Then hit ON." The trainee depresses the set-difficulty switch 7 two times. The computer 52 prompts with "Currently zero two five trials.", a short pause, then "Enter difficulty level: one beginner, two intermediate, three advanced, four expert, or five master. Then hit ON". The trainee 35 depresses the set-difficulty switch 7 one time. The computer 52 prompts with "Currently at beginner difficulty level.", a short pause then "Press ON to start test or OFF to stop."

The trainee 35 now depresses the on/start switch 4 and the computer 52 decides 74 to progress to test initialization 81. The computer 52 turns off the LEDs 13-16 and/or generates a message "Begin Test" via speaker 6. The test series begins. Decisions 82 fails and a new pseudo-random stimulus time is selected 83. The computer 52 after setting an internal timer waits until the delay time is up 84. When the delay timer expires, the computer 52 immediately resets the internal timer and presents the secondary stimulus in process 85; as a result, the stimuls LEDs 13-16 turn red. The trainee 35 processes 43 the physical stimulus 42, decides 44 it is time to strike the pad, generates motor output 45 and hits the target 18 on the pad 17. The computer 52 cycles through decision 86 until the press-button switch 19 and/or the pressure transducer 20 register a strike. When a strike registers 87, the computer 52 stops the elapsed timer 88, estimates 89 the Decide component 49, and scales 90 the resulting elapsed reaction time. The computer 52 transforms the scaled elapsed time into a vertical bar on LEDs 22-28 and/or a prompts the trainee with "Elapsed time three zero zero milliseconds" via speaker 6 and increments the trial count. Program flow 82-92 is repeatedly by the computer 52 until twenty five trials are completed by the trainee. At the end of the test, the computer 52 prompts the trainee "Average performance three zero zero milliseconds" 93, a brief pause then the power up 72 prompt is repeated. The trainee 35 either initiates another test by depressing the on/start switch 4, or the trainee ends the test session by depressing the off/stop switch 5 and the computer 52 returns to a power down state 70.

Figure 5:
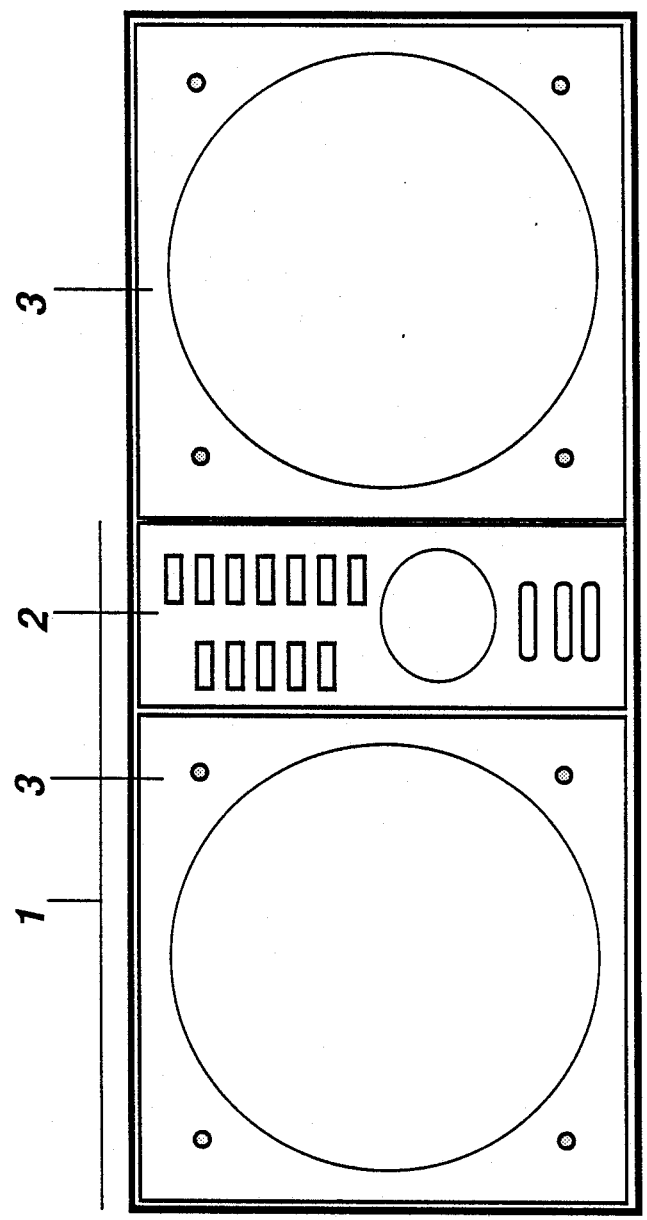
FIG. 5 shows another embodiment of the present invention with two striking pads and one controller.

Another embodiment of the invention is shown in FIG. 5. It includes a basic training unit 1 of the type shown in FIG. 1 with an additional pad unit 3. This provides a means for presenting stimuli at two different locations.

Figure 6:
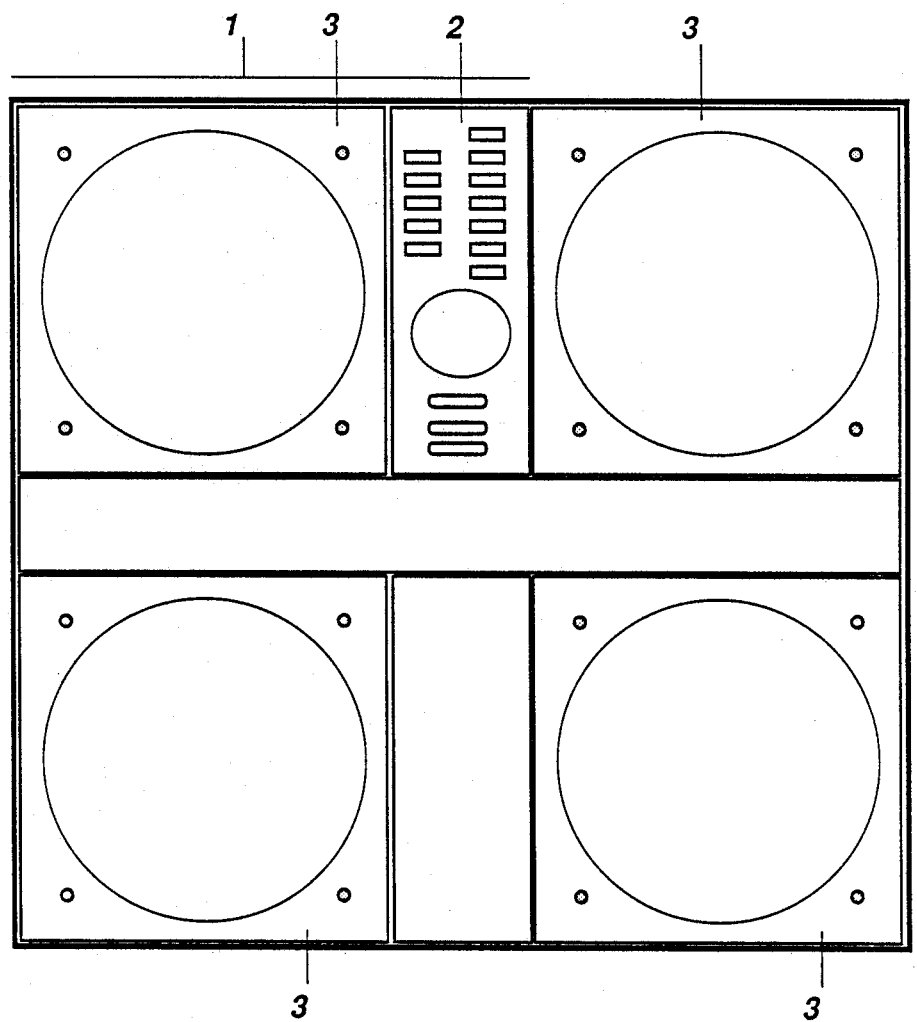
FIG. 6 shows still another embodiment of the present invention.

FIG. 6, shows another embodiment which incorporates a basic training unit 1 which is composed of a controller 2 and a pad unit 3 as in 1 FIG. 1. There are also three additional pad units 3 interfaced to the controller 2. The additional units provide stimulus at four locations.

Figure 7:
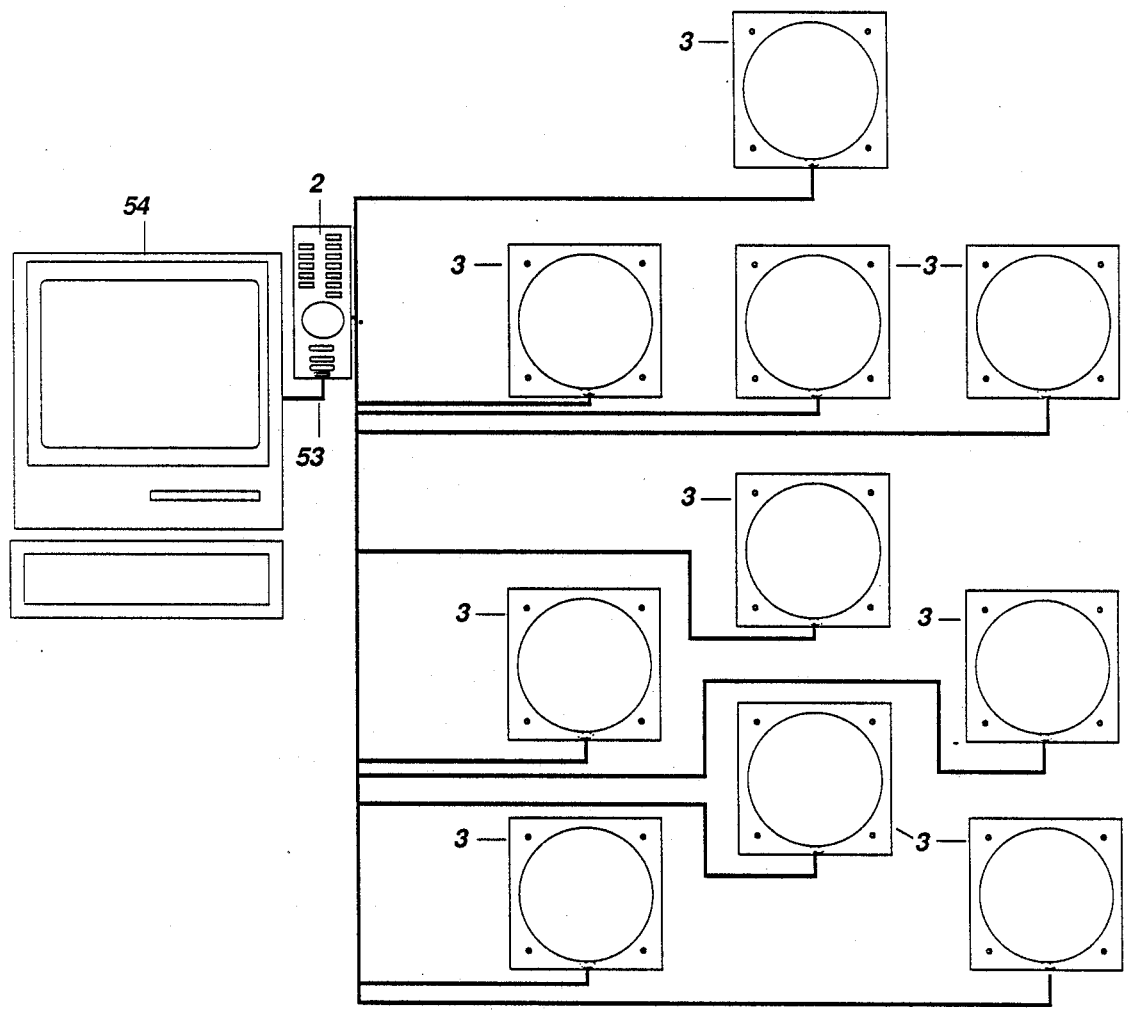
FIG. 7 shows a further embodiment of the present invention.

FIG. 7 shows an alternative embodiment. This embodiment incorporates multiple pad units 3 which are interfaced to a single controller/feedback unit 2; the latter is interfaced to a personal computer system 54 via an interface port 53. This embodiment provides a means of creating different configurations of striking targets.

The training simulator 1 FIG. 1 uses standard digital engineering techniques; see Zaks and Lesea (Microprocessor Interfacing Techniques. Berekeley: Sybex Inc. 1979) and Osborne and Kane (4 & 8-Bit Microprocessor Handbook. Berekeley: Osborne/McGraw-Hill. 1981) for microprocessor interfacing techniques. Specific information about interfacing particular microprocessor's can be found in the manufacturer's literature, such as Intel's Microcontroller Handbook (Santa Clara: Intel Corporation. 1986). Likewise, interfacing techniques about transducers are widely known, see Benedict (Fundamentals of temperature pressure and flow measurements. Stamfort CT: Omega Press. 1985), and can be found in the particular manufacturer's literature, such as Omega's 1986 Complete Pressure and Strain Measurement Handbook and Encyclopedia (Stamfort, CT: Omega Engineering, Inc. 1985).

While the present invention has been described with reference to a specific embodiment of a reaction time test of varying difficulty with audio command prompts, audio/visual feedback of multiple component reflex arc performance, the description is illustrative of the invention and is not to be construed as limiting the invention. Various modifications may occur to those skilled in the art without departing from the true spirit and scope of the invention as defined by the appended claims. In particular, measurement of reaction times under varying conditions of test difficulty with respect to pre-specified striking behavior and the segmenting of a reaction time into components to estimate performance parameters of the psychophysiological reflex arc, and the generation of audio commands/feedback in languages different from English, may be refined but remain in the true spirit of the invention.

We claim:

1. A training simulator comprising
   means for providing a reaction stimulus having at least two forms,
   means for selectively establishing a degree of difficulty,
   means for randomly energizing said reaction time stimulus to provide said different forms of stimulus in accordance with said established degree of difficulty,
   means for sensing a reaction to said energized stimulus,
   means connected to said reaction time sensing means for measuring the reaction time to said energized stimulus, and
   means for generating an indication of the measured reaction time.

2. A training simulator as in claim 1 in which said energizing means and said measuring means comprise an electronic controller.

3. A training simulator as in claim 2 wherein said sensing means and reaction time stimulus means are embodied in a unit adapted to be connected to said controller.

4. A training simulator as in claim 3 including a plurality of said units are connected to said controller.

5. A training simulator as in claim 2 in which said controller includes
   means for estimating the sense phase of reaction time
   means for estimating the action phase of said reaction time, and
   means for estimating the decide phase by subtracting the estimate of the sense and act phase from the measured reaction time with respect to a given degree of difficulty.

6. A training simulator as in claim 1 in which said means for providing a reaction time stimulus comprises at least visual stimulus means.

7. Apparatus as in claim 6 in which said means for providing a degree of difficulty comprises means for controlling the duration of said visual stimulus.

8. Apparatus as in claim 6 in which said means for providing a degree of difficulty for controlling the duration and frequency of said visual stimulus.

9. A training simulator as in claim 1 in which said means for providing a reaction time stimulus comprises at least an acoustic stimulus.

10. A training simulator as in claim 1 including means for measuring the decision phase of reaction time.

11. A training simulator as in claim 1 in which means for energizing the stimulus in accordance with the degree of difficulty provides a predefined pattern of stimuli of varying complexity as determined by the degree of difficulty.

12. A training simulator as in claim 1 in which said means for indicating the reaction time comprises a visual display.

13. A training simulator as in claim 1 in which said means for indicating the reaction time comprises an audible signaling means.

14. A training simulator as in claim 1 including means for sensing the force and providing an indication of the force of said reaction time test.

15. A training simulator as in claim 1 including means for determining whether a reaction time is valid.

16. A training simulator comprising:
   a reaction sensing unit,
   light means for providing a visual reaction stimulus having at least two forms associated with said unit,
   means for establishing a degree of difficulty and randomly energizing said light means accordingly to randomly provide said different forms of stimulus,
   means responsive to energization of said light means and sensing of reaction by said reaction sensing unit to provide a reaction time signal, and
   means responsive to said reaction time signal to provide an indication of said reaction time.

17. A training simulator as in claim 16 in which said light means provides light of at least two different colors.

18. A training simulator as in claim 16 in which said light means provides light at least two different frequencies.

19. A training simulator as in claim 16 in which said light means provides light of at least two different colors of at least two different frequencies.

* * * * *